(12) United States Patent
Gelotte et al.

(10) Patent No.: US 6,211,246 B1
(45) Date of Patent: Apr. 3, 2001

(54) RAPIDLY ABSORBED LIQUID COMPOSITIONS

(75) Inventors: Cathy Klech Gelotte, North Wales; Joanna F. Hills, Glenside; Charles E. Pendley, II, Abington; Manoj N. Shah, Norristown, all of PA (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/329,900

(22) Filed: Jun. 10, 1999

(51) Int. Cl.[7] .......................... A61K 31/135; A61K 31/19
(52) U.S. Cl. .......................... 514/653; 514/568; 514/849; 514/853
(58) Field of Search ................................... 514/653, 849, 514/853, 568

(56) References Cited

U.S. PATENT DOCUMENTS

| | | |
|---|---|---|
| 4,479,956 | 10/1984 | Sunshine et al. .................. 424/253 |
| 4,486,436 | 12/1984 | Sunshine et al. .................. 424/253 |
| 4,522,826 | 6/1985 | Sunshine et al. .................. 514/569 |
| 4,552,899 | 11/1985 | Sunshine et al. .................. 514/568 |
| 4,558,051 | 12/1985 | Sunshine et al. .................. 514/261 |
| 4,567,183 | 1/1986 | Sunshine et al. .................. 514/264 |
| 4,585,783 | 4/1986 | Sunshine et al. .................. 514/408 |
| 4,587,249 | 5/1986 | Sunshine et al. .................. 514/265 |
| 4,656,177 | 4/1987 | Sunshine et al. .................. 514/264 |
| 4,749,711 | 6/1988 | Sunshine et al. .................. 514/226.5 |
| 4,749,721 | 6/1988 | Sunshine et al. .................. 514/532 |
| 4,749,722 | 6/1988 | Sunshine et al. .................. 514/567 |
| 4,783,465 | 11/1988 | Sunshine et al. .................. 514/255 |
| 4,839,354 | 6/1989 | Sunshine et al. .................. 514/226.5 |
| 4,871,733 | 10/1989 | Sunshine et al. .................. 514/212 |
| 4,883,818 | 11/1989 | Sunshine et al. .................. 514/570 |
| 4,923,898 | 5/1990 | Sunshine et al. .................. 514/557 |
| 4,962,124 | 10/1990 | Sunshine et al. .................. 514/568 |
| 4,975,426 | 12/1990 | Sunshine et al. .................. 514/159 |
| 4,980,375 | 12/1990 | Sunshine et al. .................. 514/570 |
| 4,985,459 | 1/1991 | Sunshine et al. .................. 514/561 |
| 4,990,535 | 2/1991 | Cho et al. .......................... 514/556 |
| 5,025,019 | 6/1991 | Sunshine et al. .................. 514/277 |
| 5,075,114 | 12/1991 | Roche ............................... 424/470 |
| 5,100,918 | 3/1992 | Sunshine et al. .................. 514/557 |
| 5,215,755 | 6/1993 | Roche et al. ..................... 424/480 |
| 5,286,751 | 2/1994 | Sunshine et al. .................. 514/570 |
| 5,296,233 | 3/1994 | Batista et al. ..................... 424/463 |
| 5,373,022 | 12/1994 | Fawzi et al. ...................... 514/570 |
| 5,374,659 | * 12/1994 | Gowan, Jr. ........................ 514/557 |
| 5,385,941 | 1/1995 | Fawzi et al. ...................... 514/567 |
| 5,674,522 | 10/1997 | Shah et al. ........................ 424/439 |
| 5,712,310 | * 1/1998 | Koch ................................. 514/570 |
| 5,759,579 | * 6/1998 | Singh et al. ...................... 424/485 |
| 6,017,932 | * 1/2000 | Singh et al. ...................... 514/321 |
| B1 4,522,899 | 10/1992 | Sunshine et al. .................. 514/568 |

FOREIGN PATENT DOCUMENTS

| | | | |
|---|---|---|---|
| 0856310A2 | * 5/1998 | (EP) . | |
| WO 92/15332 | 9/1992 | (WO) | ........................ A61K/45/06 |
| PCT9632941 | * 10/1996 | (WO) . | |
| WO 98/38983 | 9/1998 | (WO) | ........................ A61K/9/20 |

OTHER PUBLICATIONS

Lemsip Power +, Patient Information Leaflet, Product Literature, 1996.

Dr. S.D. Oliver, "Pharmacokinetics and Clinical Activity of a Soluble Combination of Ibuprofen and Pseudophedrine" European Journal of Clinical Researh (1996) 8:269–280.

* cited by examiner

*Primary Examiner*—Frederick Krass
*Assistant Examiner*—Donna Jagoe

(57) ABSTRACT

The present invention provides a method which provides for a faster absorption of pharmaceutically acceptable amines. The method provides a pharmaceutically acceptable amine in combination with a non-steroidal anti-inflammatory drug in a liquid form. A preferred embodiment employs pseudoephedrine and ibuprofen.

37 Claims, 3 Drawing Sheets

RAPIDLY ABSORBED LIQUID COMPOSITIONS

FIELD OF THE INVENTION

This invention relates to medicaments that contain a combination of an analgesic/anti-inflammatory acidic compound and a pharmacologically active amine. In a preferred embodiment the present invention is related to the combination of materials in a liquid dosage form.

BACKGROUND OF THE INVENTION

Products which combine multiple pharmaceutically active ingredients are available commercially throughout the world. Consumers purchase these medicaments because they relieve several symptoms at the same time. For example, ibuprofen and pseudoephedrine are sold in combination in solid forms, such as tablets, capsules, and powders for re-constitution. Ibuprofen is an effective analgesic/antipyretic agent, whereas pseudoephedrine is an effective decongestant. The combination of these two active ingredients is particularly effective for relieving sinus headache, and symptoms of cold and flu. Ibuprofen and pseudoephedrine combinations are disclosed in U.S. Pat. No. 4,552,899.

While these products are known to be effective, consumers who use them are seeking faster symptom relief. Consequently, there continues to be a long felt need to develop products which bring rapid relief to the consumer.

Attempts have been made to improve the rate of onset of activity of various drugs by increasing their rates of absorption into the bloodstream following oral administration. For example, PCT application WO98/38983 discloses a method of improving the absorption rate of the analgesic, paracetamol, by combining it with sodium bicarbonate in a tablet or capsule formulation in a specific weight ratio. Irwin et. al. [J. Pharm. Sci. 58(3), March 1969] demonstrated enhanced absorption of the quaternary ammonium compound, isopropamide, when it was administered in combination with a large molar excess of trichloroacetate in solution. Meyer and Manning [Pharm. Res. 15(2), 1998] discuss the use of hydrophobic ion pairing to enhance the bioavailablity of poorly lipid-soluble protein and peptide drugs.

It has now been found, unexpectedly, that the absorption rate of a pharmaceutically active amine (such as pseudoephedrine) is improved when the amine is formulated together with an acidic non-steroidal anti-inflammatory drug (such as ibuprofen) in a liquid medium.

SUMMARY OF THE INVENTION

The present invention provides a method for enhancing the absorption of a pharmacologically active amine which comprises providing a pharmaceutically effective dose of the amine, and an effective dose of a non-steroidal anti-inflammatory agent together in a liquid medium to provide enhanced bio-absorption of the amine.

DETAILED DESCRIPTION OF THE INVENTION

Figure 1:
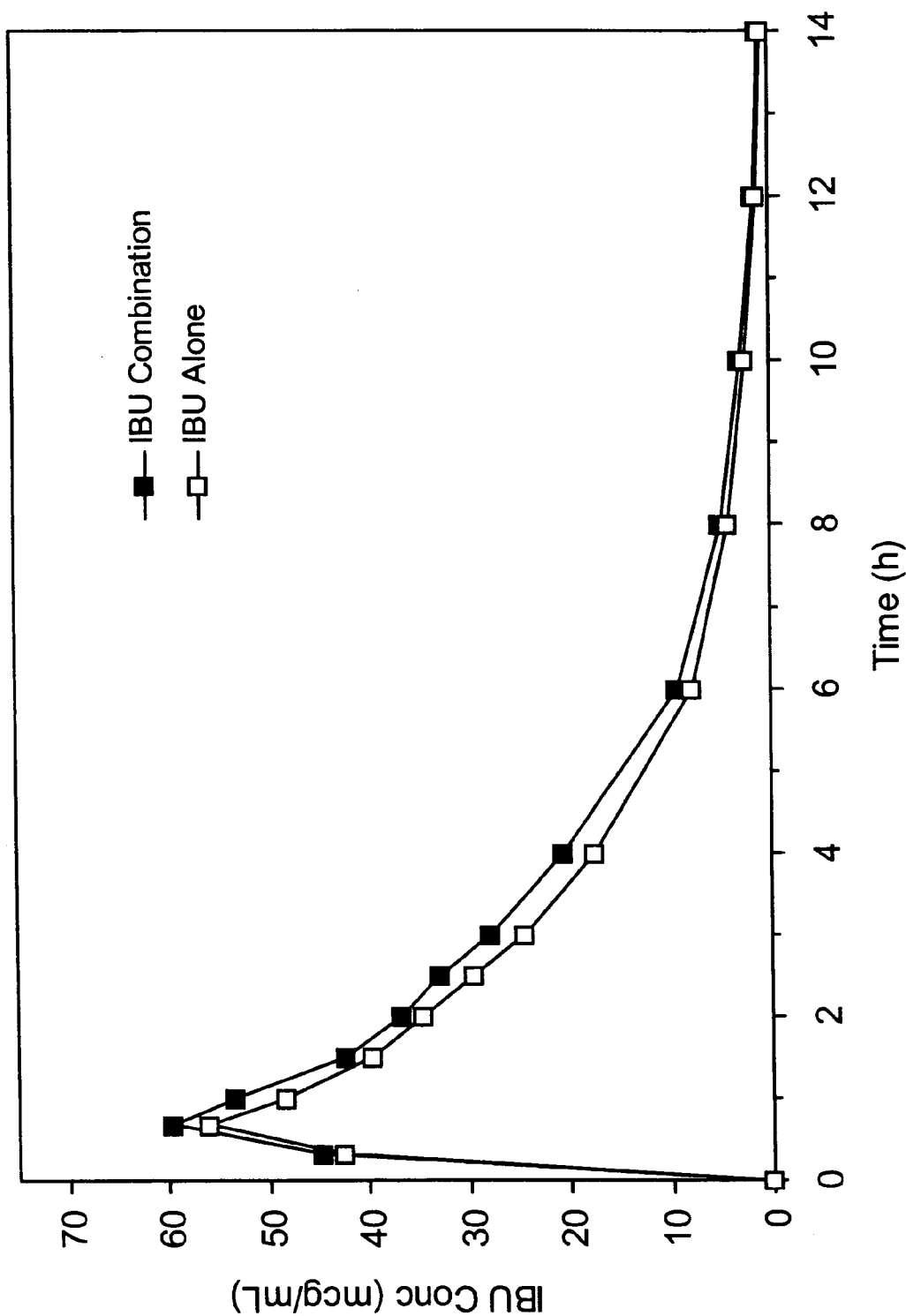
FIG. 1 shows the pharmacokinetic profiles for ibuprofen from liquid dosage forms.

The nonsteroidal anti-inflammatory drugs, commonly referred to as NSAIDs, for use in the present invention are well known in the art. They may be selected from proprionic acid derivatives, acetic acid derivatives, fenamic acid derivatives, and biphenylcarboxylic acid derivatives. Accordingly, the term NSAID as used herein is understood to mean any non-narcotic analgesic nonsteroidal anti-inflammatory compound, including pharmaceutically acceptable salts thereof which fall within the classes of compounds set forth above. The acceptable salts include sodium, potassium, arginine, lysine, and the like.

Specific examples of the propioinic acid derivatives include ibuprofen, naproxen, naproxen sodium, fenoprefen, ketoprofen and the like. Suitable acetic acid derivatives include indomethacin, zomepirac, sulindac and the like. Suitable fenamic acid derivatives include mefenamic acid and meclofenamate sodium. Suitable biphenylcarboxylic acid derivatives include diflunisal and flufenisal. The preferred NSAIDs are ibuprofen, ketoprofen and naproxen. It is understood that aspirin is not included in the definition of NSAID as used in this invention.

The dosage of the NSAID will vary according to the potency of the specific compound. Therapeutic doses for these analgesics are well known in the art and can be found in the Physician's Desk Reference (Medical Economics Company, Montvale, N.J.). The preferred dosage of NSAID is 40–800 milligrams of ibuprofen every 4 to 6 hours.

The pharmaceutically acceptable amines include primary, secondary and tertiary amines. Suitable pharmaceutically acceptable amines include pseudoephedrine, phenylpropanolamine, dextromethorphan, chlorpheniramine, diphenhydramine, loratadine, fexofenadine, and citirazine, famotidine, ranitidine, cimetidine and their pharmaceutically acceptable salts.

The dosage of the amine will vary according to the potency of the specific compound. Therapeutic doses for these analgesics are well known in the art and can be found in the Physician's Desk Reference (Medical Economics Company, Montvale, N.J.). The preferred dosage of amine is 15 to 60 milligrams of pseudoephedrine every 4 to 6 hours, with the preferred combination being 100 milligrams of ibuprofen and 15 milligrams of pseudoephedrine per 5 milliliter dosage.

The present invention contemplates the NSAID and the amine to be in any stable liquid form, which includes but is not limited to solutions, emulsions, dispersions, colloidal dispersions, suspensions, liquid-filled soft gelatin capsules, and the like. The liquids will employ suitable emulsifying, suspending, dispersing, stabilizing, or solubilizing agents and diluents that are well known in the art. As used herein, stable liquid forms are understood to be systems that maintain acceptable physical, chemical, and microbial properties for at least 30 days, preferably at least 12 months, and most preferably at least 24 months in ordinary pharmaceutical packaging under conditions encountered during normal distribution and storage of the liquid product.

The NSAID will be dissolved or suspended, but preferably suspended, whereas the amine will be substantially dissolved in the liquid medium. As used herein, suspensions are understood to be a system in which small particles are more or less uniformly dispersed in a liquid medium. The suspensions will employ suitable suspending and dispersing agents that are well known in the art, see for example U.S. Pat. No. 5,374,659 the contents of which are hereby incorporated by reference. Examples of such suspending materials include, but are not limited to, polycarbohydrates such as cellulose derivitives, starch and starch derivitives, xanthan gum, carageenan, locust bean gum, and the like, wetting agents such as sodium laurel sulfate and alkyl polyoxyethylene sulfates; sulfonates such as quaternary ammonium compounds; nonionic materials such as polyoxyethylene fatty alcohol ethers, sorbitan fatty esters and polyoxyethylene sorbitan fatty acid esters. A preferred system as disclosed in U.S. Pat. No. 5,374,659, is comprised of xantham gum, pregelatinized starch and polyoxyethylene monooleate. Further agents are set forth in Remmington's Pharmaceutical Sciences, 15$^{th}$ Edition, Osol and Hoover Editors, 1975.

The suspending agents are employed at levels of from about 0.1 to about 5 weight percent, preferably from about 0.25 to about 3 and most preferably from about 0.5 to about 2 weight percent. Water is the preferred solvent system, although any pharmaceutically acceptable solvent may be employed.

The compositions of the present invention may also contain, in addition to the NSAID and amine components, other pharmaceutically active ingredients including antihistamines, decongestants, antitussives, and expectorants. Typically these pharmaceutically active ingredients are provided in their effective dosages which are known, see for example U.S. Pat. No. 4,552,899.

The compositions of the present invention have an increased drug exposure of the amine to humans at early times after dosing, when compared with other amine compositions. Early drug exposure is measured by the area under the blood, plasma, or serum concentration curve from when the drug is swallowed until 1 or 2 hours later (AUC 1 H or AUC 2 H). Total drug exposure is the area under the curve that is extrapolated to infinite time (AUC INFINITY). A comparative study has demonstrated an increased early amine exposure (AUC 1 H and AUC 2 H) with respect to that obtained in absence of an effective amount of an NSAID in the liquid form.

The compositions of the present invention give an early amine exposure in the consumer's bloodstream for the first hour (AUC 1 H) that is about 10% higher, preferably more than about 40% higher, and most preferably more than about 80% higher than the early drug exposure of the same amine from a single-ingredient liquid product. Furthermore, compositions of the present invention give an early amine exposure in the consumer's bloodstream for the first 2 hours (AUC 2 H) that is about 10% higher, preferably more than about 20% higher, and most preferably more than about 40% higher than the early drug exposure of the same amine from a single-ingredient liquid product Furthermore, compositions according to the present invention have an increased C$_{MAX}$, where C$_{MAX}$ is the maximum concentration of the amine in blood, plasma, or serum, that occurs sooner when compared with other amine liquid compositions. This change also indicates the increased rate or enhancement of absorption of the pharmaceutically acceptable amine, as compared with amines in the absence of the NSAID. The compositions of the present invention give a maximum concentration of amine in the consumer's bloodstream about 10% higher, preferably more than about 12.5% higher, and most preferably more than about 15% higher than the maximum concentration of the same amine from a single-ingredient liquid product.

Furthermore, the compositions according to the present invention provide total amine exposure (AUC INFINITY) that is equal to that provided by amines in the absence of the NSAID, indicating that there is no decrease in the overall extent of absorption of the pharmaceutically acceptable amine.

Without wishing to be bound by any theory, the present invention is believed to function due to the formation of an ion pair in the liquid medium. This ion pairing apparently does not form with solid dosage forms. The ion pair enables the amine drugs to be delivered more efficiently and rapidly to the bloodstream, thus providing higher early drug exposure and higher maximum concentrations sooner compared with the amine in the absence of the NSAID in the liquid form or with the amine in the presence of the NSAID in a solid form. The present invention, therefore, will provide the consumer with a faster onset of activity for the pharmacologically active amine.

The following examples are provided to further illustrate the claimed invention, but not limit the invention to the examples provided below. As used herein mg is understood to mean milligrams, ng is understood to mean nanograms, kg is understood to be kilograms and ml is understood to be milliliters.

EXAMPLE 1

Twenty-four healthy subjects, 10 men and 14 women, ages 18 through 55 years, were included in a study. Subjects crossed over three treatments, and the study periods were separated by a minimum of one week for drug washout. They reported to the clinical site the evening before each study period, and remained cloistered until after the last blood sample was collected 14 hours after dosing.

Treatment A was one dose of test suspension, consisting of 7.5 mg/kg ibuprofen and 1.125 mg/kg pseudoephedrine HCl (ingredients provided in Table 1) prepared as disclosed in U.S. Pat. No. 5,621,005, example 1, additionally with pseudoephedrine HCl added after the ibuprofen addition step. Treatment B was one dose of Children's Motrin® Ibuprofen Suspension, (McNeil Consumer Healthcare) consisting of 7.5 mg/kg ibuprofen. Treatment C was one dose of Children's Sudafed® Nasal Decongestant Liquid (Warner Lambert), consisting of 1.125 mg/kg pseudoephedrine.

TABLE 1

Treatment A Suspension Formula

| Ingredients | (% w/v) |
| --- | --- |
| Glycerin USP | 10.0 |
| Xanthan Gum NF | 0.18 |
| Pregelatinized Starch | 1.5 |
| Sucrose NF | 35.0 |
| Colors | 0.0038 |
| Polysorbate 80 NF | 0.05 |
| Artificial Flavors | 0.893 |
| Ibuprofen USP | 2.0 |
| Pseudoephedrine HCL USP | 0.30 |
| Sodium Benzoate NF | 0.20 |
| Citric Acid USP | 0.18 |
| Purified Water USP | 64.2 |

After an overnight fast, subjects swallowed the product and drank six fluid ounces of water immediately. Seven milliliters of blood were before dosing and at 0.33, 0.67, 1, 1.5, 2, 2.5, 3, 4, 6, 8, 10, 12, and 14 hours after dosing. Plasma was removed from the blood samples, and was quantified for ibuprofen and pseudoephedrine separately using two specific high-performance liquid chromatography (HPLC) methods.

The following single-dose pharmacokinetic parameters for ibuprofen and pseudoephedrine in plasma were determined using noncompartmental methods: early drug exposure up to 1 hour (AUC 1 H), early drug exposure up to 2 hours (AUC 2 H), area under the plasma concentration-time curve extrapolated to infinity (AUC INFINITY), and peak plasma concentration (CMAX). The speed or rate of drug absorption are reflected by AUC 1 H, AUC 2 H, and CMAX.

Ibuprofen and pseudoephedrine parameter means were analyzed separately creating a three-period, two-treatment crossover. Means for the combination product and either ibuprofen or pseudoephedrine alone were compared by analysis of variance (ANOVA). From the ANOVA, statistically significant differences in means are detected for p values less than 0.05.

Figure 2:
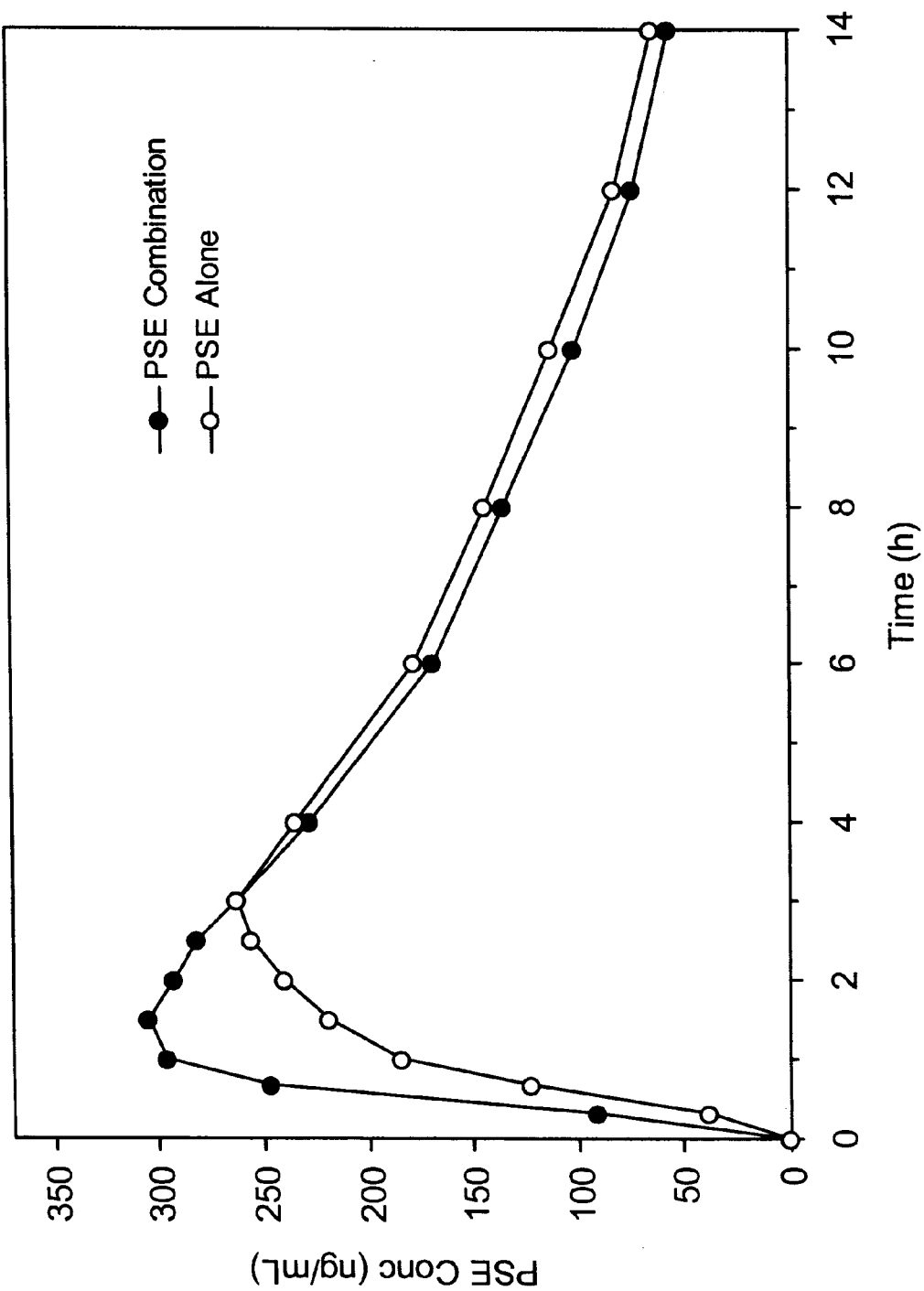
FIG. 2 shows the pharmacokinetic profiles for pseudoephedrine from liquid dosage forms.

Mean profiles of ibuprofen plasma concentrations over time for the ibuprofen-pseudoephedrine combination suspension and the Motrin® suspension are shown in FIG. 1. They are similarly shaped and virtually superimposable, indicating no change in ibuprofen absorption rate when combined with an amine. Mean profiles of pseudoephedrine for the ibuprofen-pseudoephedrine combination suspension and the Sudafed® liquid are shown in FIG. 2. The amine was absorbed at a faster rate from the combination suspension than from the marketed liquid, which is reflected by a steeper slope and higher peak concentration. This observation was unexpected, because pseudoephedrine is dissolved as the hydrochloride salt in the liquid vehicle of both products.

Results from the data analysis for pseudoephedrine are summarized in Table 2, which clearly demonstrate that the amine's absorption rate was enhanced by ibuprofen in the liquid dosage form. The example composition of the present invention increased the early amine exposure in humans by 93% over the first hour (AUC 1 H) and by 54% over the first two hours (AUC 2 H) when compared with the single-ingredient, amine liquid product. This difference was highly statistically significant, as both p values were equal to 0.0001. In addition, the average pseudoephedrine concentration in plasma from the combination liquid product peaked 18% higher and occurred one hour earlier when compared with Sudafed® liquid. Both of the latter differences were statistically significant.

TABLE 2

Pseudoephedrine (PSE) Study Results

| Parameters | SUDAFED® Liquid | IBU-PSE Suspension | Percent Difference | ANOVA p value |
| --- | --- | --- | --- | --- |
| AUC up to 1 hour (ng · h/mL) | 83.6 | 161.6 | +93% | 0.0001 |
| AUC up to 2 hours (ng · h/mL) | 299 | 461 | +54% | 0.0001 |
| AUC INFINITY (ng · h/mL) | 2633 | 2614 | −1% | NS |
| CMAX (ng/mL) | 273 | 322 | +18% | 0.0001 |

NS = not statistically significant

Comparative Example 2

Twenty-four healthy men, ages 18 through 50 years, were included in a study. Subjects crossed over four treatments, and the study periods were separated by a minimum of one week for drug washout. They reported to the clinical site the evening before each study period, and remained cloistered until after the last blood sample was collected 24 hours after dosing.

Treatment A was one combination tablet containing 200 mg ibuprofen and 30 mg pseudoephedrine. Treatment B was one Nuprin® tablet (Bristol-Meyers), containing 200 mg ibuprofen, plus one Sudafed® tablet (Warner Lambert), containing 30 mg pseudoephedrine. Treatment C was one Nuprin® tablet (Bristol-Meyers), containing 200 mg ibuprofen. Treatment D was one Sudafed® tablet (Warner Lambert), containing 30 mg pseudoephedrine.

After an overnight fast, subjects swallowed the product and drank 200 ml of water immediately. Eight milliliters of blood were collected before dosing and at 0.25, 0.5, 0.75, 1, 1.5, 2, 3, 4, 6, 8, 10, 12, and 24 hours after dosing. Plasma was removed from the blood samples and was quantified for ibuprofen and pseudoephedrine separately using high-performance liquid chromatography and gas chromatography methods, respectively.

The following single-dose pharmacokinetic parameters for ibuprofen and pseudoephedrine in plasma were determined using noncompartmental methods: early drug exposure up to 1 hour (AUC 1 H), early drug exposure up to 2 hours (AUC 2 H), area under the plasma concentration-time curve extrapolated to infinity (AUC INFINITY), and peak plasma concentration (CMAX). The speed or rate of drug absorption is reflected by AUC 1 H, AUC 2 H, and CMAX.

Ibuprofen and pseudoephedrine parameter means were analyzed separately creating a four-period, three-treatment crossover. Means for the combination product and either ibuprofen or pseudoephedrine alone were compared by analysis of variance (ANOVA). From the ANOVA, statistically significant differences in means are detected for p values less than 0.05.

Figure 3:
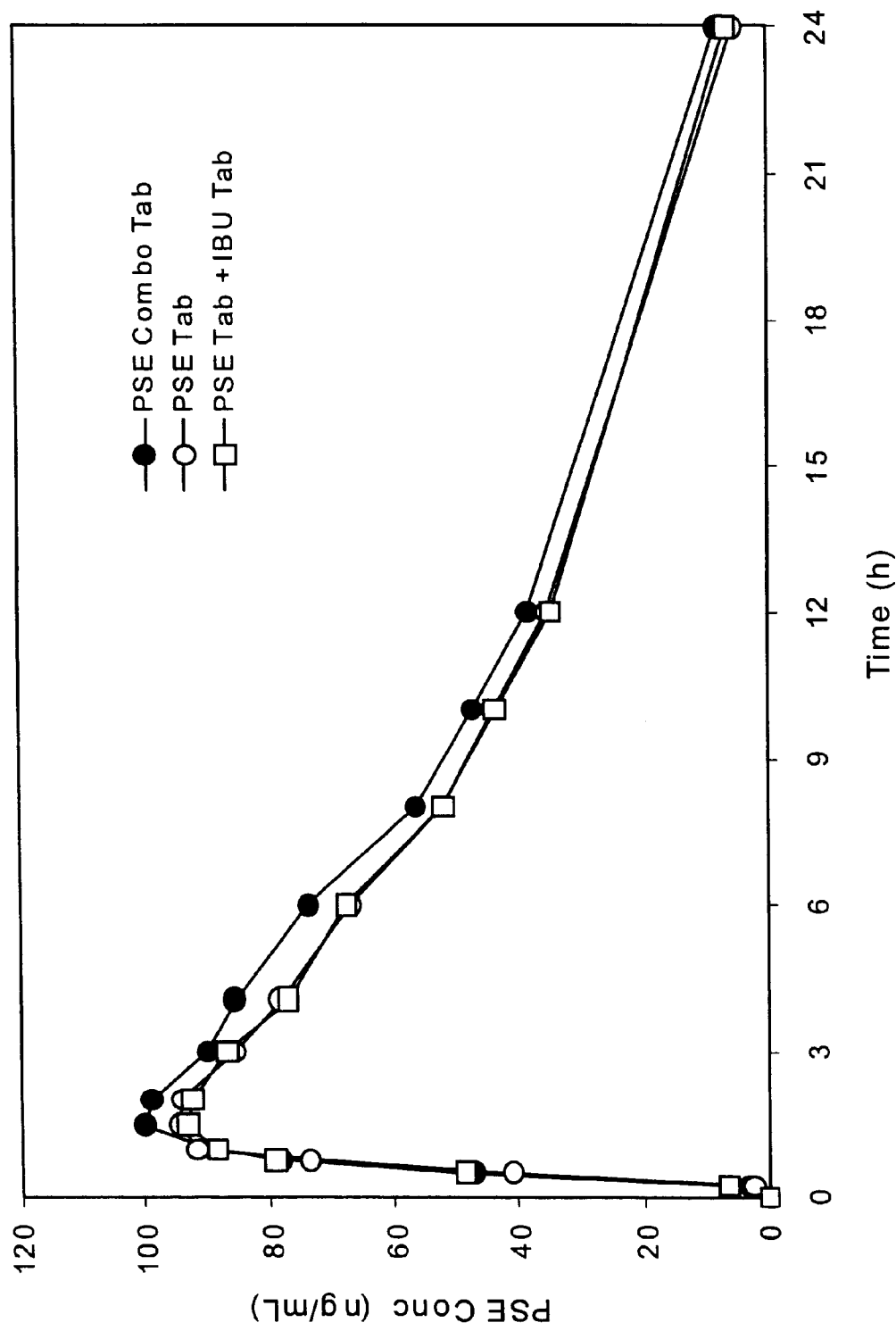
FIG. 3 shows the pharmacokinetic profiles for pseudoephedrine from solid dosage forms.

Mean profiles of pseudoephedrine for the ibuprofen-pseudoephedrine combination tablet and for the Sudafed® tablet dosed alone and with a NUPRIN® tablet are shown in FIG. 3. They are similarly shaped and virtually superimposable, indicating that ibuprofen did not change the absorption rate of pseudoephedrine when formulated in a solid dosage form.

Results from the data analysis for pseudoephedrine are summarized in Tables 3 and 4, which clearly demonstrate that the amine's absorption rate was not affected by ibuprofen when formulated as a tablet. There were no statistically significant differences between any of the following means: AUC 1 H, AUC 2 H, AUC INFINITY, and CMAX.

TABLE 3

Pseudoephedrine (PSE) Study Results Comparing Treatments A and B

| Parameters | SUDAFED® Tablet (NUPRIN) | IBU-PSE Tablet | Percent Difference | ANOVA p value |
| --- | --- | --- | --- | --- |
| AUC up to 1 hour (ng · h/mL) | 43.8 | 43.2 | −1% | NS |
| AUC up to 2 hours (ng · h/mL) | 136 | 140 | +4% | NS |
| AUC INFINITY (ng · h/mL) | 1111 | 1203 | +8% | NS |
| CMAX (ng/mL) | 102 | 107 | +5% | NS |

NS = not statistically significant

TABLE 4

Pseudoephedrine (PSE) Study Results Comparing Treatments A and D

| Parameters | SUDAFED ® Tablet (Alone) | IBU-PSE Tablet | Percent Difference | ANOVA p value |
|---|---|---|---|---|
| AUC up to 1 hour (ng · h/mL) | 40.7 | 43.2 | +6% | NS |
| AUC up to 2 hours (ng · h/mL) | 134 | 140 | +3% | NS |
| AUC INFINITY (ng · h/mL) | 1125 | 1203 | +7% | NS |
| CMAX (ng/mL) | 104 | 107 | +3% | NS |

NS = not statistically significant

We claim:

1. A method for enhancing the absorption rate of a pharmaceutically acceptable amine into the blood of a human comprising administering a pharmacologically effective dosage of a pharmaceutically acceptable amine and an effective amount of a nonsteroidal anti-inflammatory acidic drug in a stable liquid form.

2. The method of claim 1 wherein the enhanced absorption is indicated by $AUC_1 H$ (early drug exposure) that is at least about 10% higher than the early drug exposure of the same amine from a single-ingredient liquid.

3. The method of claim 1 wherein the enhanced absorption is indicated by $AUC_2 H$ (early drug exposure) that is at least about 10% higher than the early drug exposure of the same amine from a single-ingredient liquid.

4. The method of claim 1 wherein the enhanced absorption is indicated by a $C_{MAX}$ (maximum or peak concentration) that is at least about 10% greater than the $C_{MAX}$ of the same amine from a single-ingredient liquid.

5. The method of claim 1 wherein the stable liquid form is a suspension.

6. The method of claim 1 wherein the amine is pseudoephedrine.

7. The method of claim 1 wherein the nonsteroidal anti-inflammatory drug is ibuprofen.

8. The method of claim 6 wherein the pseudoephedrine is provided in a range from about 15 mg to about 60 mg per dosage unit.

9. The method of claim 6 wherein the pseudoephedrine is provided in a range from about 15 mg to about 45 mg per dosage unit.

10. The method of claim 7 wherein the ibuprofen is provided in an amount of from about 40 mg to about 800 mg per dosage unit.

11. The method of claim 7 wherein the ibuprofen is provided in an amount of from about 40 mg to about 300 mg per dosage unit.

12. The method of claim 1 wherein the amine is pseudoephedrine at about 15 milligrams and the nonsteroidal anti-inflammatory is ibuprofen provided at a level at about 100 milligrams per 5 mL.

13. The method of claim 1 wherein the human is a child.

14. A composition comprising a pharmacologically effective amount of a pharmaceutically acceptable amine and a pharmacologically effective amount of a nonsteroidal anti-inflammatory drug, wherein said amine and nonsteroidal anti-inflammatory drug are provided in a stable liquid suspension, said suspension comprised of xanthan gum, pregelatinized starch, polyoxyethylene sorbitan monooleate and a taste masking agent selected from the group consisting of sugar, sweet polyhydric alcohol, cyclamates, aspartame, sucralose saccharin, flavoring agents and mixtures thereof, wherein the composition provides an enhanced absorption rate of the amine into the blood of a human compared with a corresponding composition comprising the amine but not the nonsteroidal anti-inflammatory drug.

15. The composition of claim 14 wherein the stable liquid form is a suspension.

16. The composition of claim 14 wherein the nonsteroidal anti-inflammatory drug is ibuprofen and the pharmaceutically acceptable amine is pseudoephedrine.

17. The composition of claim 16 wherein the ibuprofen is provided at dosage of about 100 milligrams and the pseudoephedrine is provided at a dosage of about 15 milligrams per 5 mL.

18. The composition of claim 16 where the pseudoephedrine is provided in a range from about 15 mg to about 60 mg per dosage unit.

19. The composition of claim 16 where the ibuprofen is provided in a range from about 40 mg to about 800 mg per dosage unit.

20. The composition of claim 16 wherein the enhanced absorption is indicated by $AUC_1 H$ that is at least about 10% higher than the early drug exposure of the same amine from a single-ingredient liquid.

21. The composition of claim 16 wherein the enhanced absorption is indicated by $AUC_2 H$ that is at least about 10% higher than the early drug exposure of the same amine from a single-ingredient liquid.

22. The composition of claim 16 wherein the enhanced absorption is indicated by a $C_{MAX}$ that is at least about 10% greater than the $C_{MAX}$ of the same amine from a single-ingredient liquid.

23. A stable liquid composition comprising a pharmacologically effective amount of a pharmaceutically acceptable amine and a pharmacologically effective amount of a nonsteroidal anti-inflammatory drug, wherein the composition provides an enhanced absorption rate of the amine into the blood of a human compared with a corresponding composition comprising the amine but not the nonsteroidal anti-inflammatory drug.

24. The composition of claim 23 wherein the nonsteroidal anti-inflammatory drug is ibuprofen and the pharmaceutically acceptable amine is pseudoephedrine.

25. The composition of claim 23 wherein the ibuprofen is provided at dosage of about 100 milligrams and the pseudoephedrine is provided at a dosage of about 15 milligrams per 5 mL.

26. The composition of claim 23 where the pseudoephedrine is provided in a range from about 15 mg to about 60 mg per dosage unit.

27. The composition of claim 23 where the ibuprofen is provided in a range from about 40 mg to about 800 mg per dosage unit.

28. The composition of claim 23 wherein the enhanced absorption is indicated by $AUC_1 H$ that is at least about 10% higher than the early drug exposure of the same amine from a single-ingredient liquid.

29. The composition of claim 23 wherein the enhanced absorption is indicated by $AUC_2 H$ that is at least about 10% higher than the early drug exposure of the same amine from a single-ingredient liquid.

30. The composition of claim 23 wherein the enhanced absorption is indicated by a $C_{MAX}$ that is at least about 10% greater than the $C_{MAX}$ of the same amine from a single-ingredient liquid.

31. The method of claim 1 wherein the stable liquid form is provided in a soft gelatin capsule.

32. The method of claim 7 wherein the stable liquid form is provided in a soft gelatin capsule.

33. The method of claim 10 wherein the stable liquid form is provided in a soft gelatin capsule.

34. The composition of claim 14 wherein the suspension is provided in a soft gelatin capsule.

35. The composition of claim 19 wherein the suspension is provided in a soft gelatin capsule.

36. The composition of claim 23 wherein the stable liquid form is provided in a soft gelatin capsule.

37. The composition of claim 24 wherein the stable liquid form is provided in a soft gelatin capsule.

\* \* \* \* \*